US007005135B2

(12) United States Patent
Janas et al.

(10) Patent No.: US 7,005,135 B2
(45) Date of Patent: Feb. 28, 2006

(54) GLASS SCAFFOLDS WITH CONTROLLED RESORPTION RATES AND METHODS FOR MAKING SAME

(75) Inventors: Victor F. Janas, Monroe Township, NJ (US); Kevor S. Tenhuisen, Clinton, NJ (US)

(73) Assignee: Ethicon Inc., Somerville, NJ (US)

( * ) Notice: Subject to any disclaimer, the term of this patent is extended or adjusted under 35 U.S.C. 154(b) by 335 days.

(21) Appl. No.: 10/377,153

(22) Filed: Feb. 28, 2003

(65) Prior Publication Data

US 2003/0198660 A1 Oct. 23, 2003

Related U.S. Application Data

(63) Continuation-in-part of application No. 09/772,363, filed on Jan. 30, 2001, now abandoned.

(51) Int. Cl.
*A61F 13/00* (2006.01)
*A61F 2/00* (2006.01)
*A61J 7/00* (2006.01)
*C03C 6/00* (2006.01)

(52) U.S. Cl. .................. 424/422; 424/423; 424/426; 514/953; 514/955; 501/27; 606/77

(58) Field of Classification Search ............... 424/422, 424/423, 400; 514/953, 955; 604/891.1; 606/77; 501/27
See application file for complete search history.

(56) References Cited

U.S. PATENT DOCUMENTS

| | | | |
|---|---|---|---|
| 3,640,827 A | 2/1972 | Lutz | |
| 3,897,236 A | 7/1975 | Roberts | |
| 3,922,155 A | 11/1975 | Broemer et al. | |
| 3,930,833 A | 1/1976 | Roberts | |
| 3,958,973 A | 5/1976 | Roberts | |
| 3,981,736 A | 9/1976 | Broemer et al. | |
| 4,123,248 A | 10/1978 | Drake | |
| 4,131,597 A | 12/1978 | Bluethgen et al. | |
| 4,148,623 A | 4/1979 | Drake | |
| 4,202,055 A | 5/1980 | Reiner et al. | |
| 4,222,128 A | 9/1980 | Tomonaga et al. | |
| 4,308,064 A | 12/1981 | Takami et al. | |
| 4,329,743 A | 5/1982 | Alexander et al. | |
| 4,350,675 A | 9/1982 | Drake | |
| 4,376,168 A | 3/1983 | Takami et al. | |
| 4,392,828 A | 7/1983 | Ehrnford | |
| 4,417,912 A | 11/1983 | Abe | |
| 4,437,192 A | 3/1984 | Fujiu et al. | |
| 4,482,541 A | 11/1984 | Telfer et al. | |
| 4,604,097 A | 8/1986 | Graves, Jr. et al. | |
| 4,608,350 A | 8/1986 | Howard, Jr. | |
| 4,612,923 A | 9/1986 | Kronenthal | |
| 4,613,577 A | 9/1986 | Tagai et al. | |
| 4,645,749 A | 2/1987 | Drake | |
| 4,655,777 A | 4/1987 | Dunn et al. | |
| 4,678,659 A | 7/1987 | Drake et al. | |
| 4,735,857 A | 4/1988 | Tagai et al. | |
| 4,781,183 A | 11/1988 | Casey et al. | |
| 4,820,573 A | 4/1989 | Tagai et al. | |
| 4,847,219 A | 7/1989 | Boatner et al. | |
| 4,851,046 A | 7/1989 | Low et al. | |
| 4,867,779 A | 9/1989 | Meunier et al. | |
| 4,940,677 A | 7/1990 | Beall et al. | |
| 5,013,323 A | 5/1991 | Kobayashi et al. | |
| 5,055,428 A | 10/1991 | Porter | |
| 5,071,795 A | 12/1991 | Beall et al. | |
| 5,108,957 A | 4/1992 | Cohen et al. | |
| 5,122,484 A | 6/1992 | Beall et al. | |
| 5,215,563 A | 6/1993 | LaCourse et al. | |
| 5,250,488 A | 10/1993 | Thelohan et al. | |
| 5,252,523 A | 10/1993 | Beall et al. | |
| 5,332,699 A | 7/1994 | Olds et al. | |
| 5,401,693 A | 3/1995 | Bauer et al. | |
| 5,429,996 A | 7/1995 | Kaneko | |
| 5,468,544 A | 11/1995 | Marcolongo et al. | |
| 5,486,359 A | 1/1996 | Caplan et al. | |
| 5,609,660 A | 3/1997 | Francis et al. | |
| 5,645,934 A | 7/1997 | Marcolongo et al. | |
| 5,721,049 A | 2/1998 | Marcolongo et al. | |
| 5,770,417 A | 6/1998 | Vacanti et al. | |
| 5,843,854 A | 12/1998 | Karppinen et al. | |
| 5,984,966 A | 11/1999 | Kiema et al. | |
| 6,517,857 B1 * | 2/2003 | Ylanen et al. | ............ 424/422 |

OTHER PUBLICATIONS

Lin et al (Development of bioabsorbable glass fibres, Biomaterials 1994).*
Ropp (Inorganic Polymeric Glasses, vol. 15 pp 1-266 and 304-313).*
An article entitled "Inorganic Polymeric Glasses", by R.C. Ropp, Studies in Inorganic Chemistry, vol. 15 pp. ix-xii, 87-266, and pp. 304-313, 1992.

(Continued)

*Primary Examiner*—Gary Kunz
*Assistant Examiner*—Sharmila S. Gollamudi

(57) ABSTRACT

The present invention relates to resorbable glass scaffolds for use in biological applications and methods for making same. Specifically, these scaffolds are composed of phosphate glass fibers, where the rate of dissolution into biological fluids is controlled by the length of time the glass is held above its melt temperature prior to spinning the fiber.

14 Claims, No Drawings

OTHER PUBLICATIONS

An article entitled "Structure and Chemistry of the Apatites and Other Calcium Orthophosphates", by J.C. Elliot, Studies in Inorganic Chemistry, vol. 18, 1994.

An article entitled "Development of Bioabosorable Glass Fibres", by Steve T. Lin, Steve L. Krebs, Sudha Kadiyala, Kam W. Leong, William C. LaCourse and Binod Kumar, (1994).

An article entitled "Effect of Annealing Temperature on the Degradation of Reinforcing Fibres for Aborbable Implants", by Jack Choueka, Jose Luis Charvet, Harold Alexander, Young H. Oh, Gary Joseph, Norman C. Blumenthal and William C. LaCourse, vol. 29, 1309-1315, (1995).

An article entitled "Biodegradation and Bioresorption of Clacium Phosphate Ceramics" by Raquel Z. LeGeros, Dec. 1991.

An article entitled "Bone Graft and Bone Graft Substitutes: A Review of Current Technology and Applications" by Christopher J. Damien and J. Russell Parsons, vol. 2, 187-208, (1991).

* cited by examiner

GLASS SCAFFOLDS WITH CONTROLLED RESORPTION RATES AND METHODS FOR MAKING SAME

CROSS REFERENCE TO RELATED APPLICATION

This application is a continuation-in-part of commonly owned U.S. application Ser. No. 09/772,363 entitled "Glass Scaffolds With Controlled Resorption Rates and Methods for Making Same" and filed on Jan. 30, 2001 now abandoned.

FIELD OF THE INVENTION

The present invention relates to resorbable glass scaffolds for use in biological applications. Specifically, this invention relates to novel scaffolds, composed of resorbable glass with a tuned rate of resorption, and useful as biological replacements for hard tissue.

BACKGROUND OF THE INVENTION

Bone grafts in the form of non-woven, woven, braided, or knitted synthetic calcium phosphates (CaP) show potential as a resorbable scaffolding supporting the growth of new bone in applications such as spinal fusion, long bone fractures, non-union fractures, bone defects, and hip revisions. In known devices, the rate at which the device resorbs in the body is typically controlled by the surface area or composition of the graft. The ability to control the resorption rate of the scaffold by orders of magnitude without having to change the scaffold's composition or morphology may be advantageous in optimizing bone growth into the scaffold.

Bone grafts are used in the repair of significant fractures, the treatment of skeletal tumors, spinal fusion, and the reconstruction of failed total arthroplasties. Autogenous bone, or autograft, is harvested from another location in the patient, and used as the graft. Autograft performs very well in the applications cited above. The disadvantages of autograft include the limited supply of excess bone in the patient, as well as the inherent risks of morbidity and recovery pain resulting from a second surgery site. Allograft, bone taken from another human, has the advantage of being in larger supply than autograft bone. However, the greater immunogenic response of allograft, and risk of viral contamination or risk of transmission of live virus to the recipient, have led to the decline in use of allograft bone as a bone graft material. Xenograft, or bone grafts taken from another species, often elicits acute antigenic responses. In the vast majority of cases, xenograft fails in its role as a graft material.

Synthetic bone graft materials have been described in "Bone Graft and Bone Graft Substitutes: A Review of Current Technology and Applications"; Damien and Parsons; *J. Applied Biomaterials*, Vol. 2, 1991, pages 187–208, which is incorporated herein by reference. The ideal graft should be able to support a load equivalent to the bone that is being replaced, so that the newly formed bone can remodel to the same quality and dimensions of the original bone that is being replaced. The ideal graft is also osteoactive, enhancing the formation of new bone. This is achieved both by the chemical nature of the material, as well as the structure, or architecture of the graft. Structurally, the graft needs to be porous to allow for ingrowth of the new bone. Though no optimal pore size has been established, the size of the pores required for good bone growth is between 100 and 500 microns. The ability to tailor the pore size and distribution is also viewed as a method of enhancing bone growth. In addition, the ideal graft material will be resorbed into the body at a rate equivalent to the rate at which the new bone is being formed. If the graft resorbs too rapidly, gaps and/or stress concentrations can result. If the resorption rate is too slow, the graft may inhibit the formation of new bone.

Bone grafts come in a variety of physical forms. These include, but are not limited to, loose particles, particles bound in polymer or other carrier material (a paste), ceramic precursors that react when blended together (calcium phosphate cements), porous solids, loose fiber constructs (such as felts), or textile processed fibers (weaves, braids, or knits).

The disadvantages of using loose particles as a bone graft include the tendency of the particles to either migrate away from the defect site in bodily fluids, or settle (or pack tightly) into the defect. Particle migration from the site results in possible tissue irritation and undesired tissue response in the regions where the particles eventually settle. Particle settling results in two issues. First, when the particles pack together, the pore size is reduced in the graft to less than 100 $\mu$m. This pore size does not allow the migration and ingrowth of cells into the graft. Particle settling also results in an inability to control the pore size and distribution in these systems. The size of the particles and how they pack together determine the size and distribution of pores in these types of grafts. Since settling is not controllable, there is no ability to use graft architecture to control new bone growth into the graft.

Particle migration and settling problems have been mitigated to some extent by the use of synthetic or natural matrix materials, including polymers such as PMMA, polysulfone (PS), or polyethylene (PE), which are not resorbable, and ceramics, such as plaster of Paris. Particles have also been enclosed in tubes of resorbable polymers, such as collagen or polyglycolide. The size and distribution of pores in these types of grafts are also not controllable. The size of the particles, how they pack together, and the space between them caused by the carrier matrix determine the distribution. As with loose particles, there is limited ability to use graft architecture to control new bone growth into the graft.

For bone grafts in the form of cements, there is also a limited ability to control the pore size and distribution. Pore creating agents may be put into the cement prior to its formation. However, the size and distribution of pores are determined by the size, form, and concentration of the agent, resulting in the inability to use graft architecture to control new bone growth into the graft. This inability to control pore size and distribution also results in limits in load support capability. A random distribution of pores results in a random distribution of defects in the structure and associated low load support capability.

Control of the pore size and distribution in porous solid bone grafts is also limited. Porous solid bone grafts have been formed using the replamine process on naturally occurring coral. Here, the pore size and distribution are limited to that of the species of coral used. Defect location is also uncontrollable, lowering the load support capability of the graft in a fashion similar to that discussed above for cements. Pore creating agents may also be put into a ceramic prior to its formation. However, as is the case with cements, the size, form, and concentration of the agent determine the size and distribution of pores.

Bone grafts in the form of textile architectures, such as weaves, braids, or knits, have advantages over the other forms of bone grafts. Textile technology may by used to precisely place the fibers in a desired location in space, allowing for a large degree of control in the size and distribution of pores in the bone graft structure.

Tagai et al., in U.S. Pat. Nos. 4,820,573, 4,735,857, and 4,613,577, disclose a glass fiber for the filling of a defect or hollow portion of a bone. In this case, the calcium phosphate glass fiber may be in the form of short fibers, continuous fiber, or woven continuous fibers.

Though bone grafts in the textile forms address the limitations of particulate or solid bone grafts, one area not addressed is that of graft resorption rate. As described above, an ideal graft material will be resorbed into the body at a rate equivalent to the rate at which the new bone is being formed. Fast or slow resorption results may inhibit the formation of new bone or create gaps and/or stress concentrations in the native tissue.

An implant that slowly disappears and is replaced by native tissue, is said to be resorbed into the body. This resorption is a biological process in which the body breaks down a material into simpler components either chemically or physically. These simpler components are either soluble in bodily fluids, or digestible in cells such as macrophages. The degradation products are chemical compounds that are not toxic, and can easily be incorporated into the structure of the body or excreted.

The effects of both biological and physiochemical material properties of calcium phosphate ceramics on the rate at which bone grafts are resorbed into the body has been described in "Biodegradation and Bioresorption of Calcium Phosphate Ceramics"; Legeros; *Clinical Materials*, Vol. 14, 1993, pages 65–88, which is incorporated herein by reference. Biological factors affecting the degree and rate of resorption include age, implantation site, metabolic activity, diseased states, and the types of cells involved. The physiochemical parameters that affect resorption include the factors affecting the extent of material dissolution, such as physical form, density, porosity, composition and crystallinity.

A key parameter for determining the effect of physical form on the rate at which the graft is resorbed is the ratio of the surface area of the graft to its volume. For a given composition, as the surface to volume ratio increases, the resorption rate increases. For example, a porous graft will resorb significantly faster than a solid graft of equivalent volume. Fine particles resorb at a higher rate than course particles. A loosely woven fibrous structure resorbs at a higher rate than a tightly knitted structure of the same volume.

In U.S. Pat. No. 5,429,996, Kaneko disclosed a glass fiber/wool bone graft composed of $SiO_2$—$NaO_2$—$CaO$—$B_2O_3$—$CaF_2$—$P_2O_5$, where dissolution rate is controlled by the diameter of the glass fiber. This graft was demonstrated to work in the treatment of periodontal disease. U.S. Pat. No. 4,867,779 (Meunier et al.) discussed a particulate or fibrous glass agricultural product composed of $SiO_2$—$K_2O$—$CaO$—$MgO$—$Fe_2O_3$—$B_2O_3$—$MnO$—$ZnO$—$CuO$—$MoO_3$—$Na_2O$—$Al_2O_3$—$P_2O_5$—$SO_3$, where dissolution rate is controlled by th specific surface area of the fibers or particles. The preferred embodiment of their invention stated a most preferable specific surface area of 0.3 $m^2/gm$. The limit of both of these concepts is the difficulty involved in making the number of sizes required to control dissolution rate over a wide range.

The rate at which bone grafts are resorbed into the body is also a function of the composition of the material composing the graft. There is a great deal of prior work discussing compositional effects on dissolution rate in calcium phosphate ceramics and glasses. A good review for ceramics is found in *Structure and Chemistry of Apatites and Other Calcium Orthophosphate*; Elliot; *Studies in Inorganic Chemistry*, Vol. 18, 1994. For phosphate glasses, a review can be found in *Inorganic Calcium Phosphate glasses*; Ropp; *Studies in Inorganic Chemistry*, Vol. 15, 1992. Both reviews are incorporated herein by reference.

In U.S. Pats. Nos. 3,897,236, 3,930,833, and 3,958,973, (all to Roberts), both the rate of ion release and the solubility of soil feed glasses composed of a variety of metal oxides are controlled by the level of some of the metal oxides in the glass. These include $SiO_2$, $K_2O$, $CaO$, $B_2O_3$, and $Na_2O$.

Drake, in a series of patents (U.S. Pat. Nos. 4,123,248, 4,148,623, and 4,350,675), disclosed controlled release glass fertilizers composed of oxides of alkaline, Group II & Group III metals and $P_2O_5$. In these glasses, the release of nutrients was controlled by the rate of dissolution of the glass, which in turn was controlled by the weight percents of the components of the glass. In U.S. Pat. No. 4,645,749, Drake discussed $CaO$—$Na_2O$—$P_2O_5$ glasses for the preparation of analytical solutions, where the release of sodium ions is controlled by the ratio of calcium to phosphorous in the glass. Finally, Drake and Brocklehurst, in U.S. Pat. No. 4,678,659, disclosed a therapeutic device for oral administration to the alimentary canal, composed of soluble phosphate glasses. Here, the solubility of the glass is controlled by the ratio of metal oxides composing the glass, and is tailored to be more soluble in low pH conditions, and less soluble at higher pH conditions.

Other disclosures of water soluble phosphate-based glasses for biological application, include U.S. Pat. Nos. 5,721,049, 5,645,934, and 5,468,544 (all to Marcolongo et al.), U.S. Pat. Nos. 5,252,523, 5,071,795, and 4,940,677 (all to Beall et al.), U.S. Pat. No. 4,612,923, (to Kronenthal), U.S. Pat. No. 4,482,541, (to Telfer et al.), and U.S. Pat. No. 4,437,192, (to Fujia et al.). In each case, the rate at which the glass body breaks down, or dissolves, is controlled by the ratio of the metal oxides in the compositions.

Still other works cite water soluble mineral or glass fibers for use as degradable insulation or fireproofing, where dissolution rate is controlled by the ratio of the metal oxides in the compositions. These include phosphate-based compositions, such as disclosed in U.S. Pat. No. 5,843,854, (to Karppinen et al.), U.S. Pat. No. 5,250,488, (to Theolan et al.), and U.S. Pat. No. 5,108,957, (to Cohen et al.), as well as nonphosphate-based compositions, such as U.S. Pat. No. 5,401,693, (to Bauer et al.), U.S. Pat. No. 5,332,699, (to Olds et al.), and U.S. Pat. No. 5,055,428, (to Porter).

In all of the above cited disclosures, the composition was used as a method of controlling the rate of dissolution. The limitation of this approach in the development of bone graft materials with controlled pore size and distribution is that if one desires to have grafts with a number of different dissolution rates, one is required to melt and spin a large number of different material compositions. The different material compositions have associated different degrees of biocompatibility, creating a situation in which a material composition having a less than optimal biocompatibility may be selected in order to achieve a desired dissolution rate.

The atmosphere under which the materials have been melted is also known to alter the dissolution rate of phosphate-based glasses and glass-ceramics. In U.S. Pat. No. 5,609,660, (to Francis et al.), the dissolution rate of magnesium phosphate glass was reduced by a factor of two by exposing the glass, in particulate form, to a nitriding environment. U.S. Pat. No. 5,215,563 (to LaCourse et al.)

teaches that by melting an iron phosphate glass under a high oxygen environment, the dissolution rate can be reduced by thirty-three percent. Though these concepts are an improvement over the earlier methods of altering the composition of the glass, the range of dissolution rates possible from these teachings is small. In the present invention, resorption rates over a wide (order of magnitude) range are made possible by altering a step in the glass fiber processing.

Control of dissolution rates in phosphate glasses have also been seen by changing the stress state of the glass. This has been shown in U.S. Pat. No. 3,640,827 (to Lutz), where the dissolution rate of 9-mm spheres of sodium phosphate glass was changed by an order of magnitude by heat treating the glass below its melting point (annealing). Although Lutz '827 teaches that an order of magnitude change in dissolution can be achieved by annealing, it is limited to glass forms with dimensions significantly greater than those of interest in forming fibrous scaffolds composed of phosphate glass fibers with diameters on the order of 1–50 $\mu$m. Choueka et al., in "Effect of Annealing Temperature on the Degredation of Reinforcing Fibers for Absorbable Implants"; *J. Applied Biomaterials*, Vol. 2, 1991, pages 187–208, which is incorporated herein by reference, reports that the dissolution rate of a CaO—ZnO—$Fe_2O_3$—$P_2O_5$ glass fibers (10–20 $\mu$m in diameter) can be reduced by half by annealing below the melt temperature.

Finally, Ropp, in *Inorganic Calcium Phosphate Glasses; Studies in Inorganic Chemistry*, Vol. 15, 1992, teaches that for phosphate glasses, an increase in the time that the glass is held above its melt temperature results in an decrease in the dissolution rate of the glass by up to an order of magnitude. Ropp's work was done with cast glass bars, not fine (<100 $\mu$m diameter) glass fibers fabricated by melt drawing and pulling which are incorporated in bone graft textiles.

In summary, the prior art presents a number of synthetic bone grafts. The only grafts with tailored pore size and distributions are those composed of fibers formed into scaffold structures by textile operations. Tailored pore size is viewed as a method of enhancing bone growth. The effects of both biological and physiochemical material properties of calcium phosphate ceramics on the rate at which bone grafts are resorbed into the body have also been discussed. A known method of altering the resorption rate by an order of magnitude or more is by changing the composition of the scaffold. The ability to control the resorption rate of the scaffold by orders of magnitude without having to change the composition of the glass fibers composing the scaffold would be advantageous in matching the rate of bone growth into the scaffold with the dissolution of the scaffold.

It is therefore an object of the present invention to provide a bone graft in which the pore size and distribution are tailored to enhance bone growth, and the resorption rate of the scaffold is controlled over orders of magnitude by a simple and economical method.

Another object of this invention is to create structures to use as scaffolds for the in vitro or in vivo growth of human or animal tissue, such as bone or cartilage. These scaffolds can be used as implant materials for the replacement of defects or hollow portions of hard tissue resulting from external injury or surgical removal of hard tissue tumors. Their composition can be tailored such as to be resorbed by the body at a rate equivalent to the rate at which natural hard tissue grows into the above mentioned defects or hollow portions of hard tissue.

A still further object of this invention is the formation of laminated bioresorbable structures where each layer has controlled pore size and distribution for providing another degree of control for optimizing bone growth into the resorbable ceramic structure if the structure is used as bone graft.

SUMMARY OF THE INVENTION

The limitations of the prior art are addressed by the present invention which includes a method for making a hard tissue scaffold having resorbable glass fibers and a corresponding product. In accordance with the method, a glass composition is selected and melted to yield a glass in a melted state. The glass is maintained in a melted state for a selected time to control the resorption rate of the glass and then formed into fibers.

DETAILED DESCRIPTION OF THE INVENTION

The present invention relates to novel bone implants and their use in bone repair and reconstruction, and more particularly, to resorbable phosphate-based fibrous scaffolds with tailored rates of resorption. In the present invention, resorbable phosphate fibrous scaffolds are formed having a wide range of resorption rates. The tailoring of resorption rates is made possible by altering a step in the glass fiber processing. Therefore, a wide range of composition is not required. In the current invention, previously reported processing techniques to control the dissolution rate of phosphate glasses are combined with textile techniques to yield bioresorbable glass structures for use as bone grafts. More specifically, in the present invention, a novel hard tissue scaffold is disclosed. The size and distribution of interconnected pores in the structure are controlled, as is the rate of resorption of the scaffold. This is done by creating a woven phosphate structure, where the individual filaments are on the order of 1–100 $\mu$m.

The process for forming the scaffolds starts with commercially available analytical grades of metal salts, such as, acetates, nitrates, oxides, hydroxides or carbonates, such as CaO, $Fe_2O_3$, $Na_2O$, $K_2O$, MgO, $Al_2O_3$, $B_2O_3$, MnO, ZnO, CuO, $MoO_3$, $SiO_2$, and phosphorus-containing materials, such as phosphates, pyrophosphates or metaphosphates. The technique of spinning degradable glass compositions is discussed in U.S. Pat. No. 4,604,097 (to Graves et al.), which is incorporated herein by reference. The oxides and phosphates are weighed to obtain a predetermined ratio, mixed thoroughly, and melted in a container, or crucible that is made of materials ideally inert to the melt. A key to this invention is the amount of time that the melt is held prior to being spun into fibers. As discussed in the previously mentioned *Inorganic Calcium Phosphate Glasses; Studies in Inorganic Chemistry*, Vol. 15, 1992, Ropp teaches that an increase in the time that a phosphate glass is held above its melt temperature results in an decrease in the dissolution rate of the glass by up to an order of magnitude. Ropp's work was done in cast glass bars. In accordance with the present invention, the concept is extended to fine (<100 $\mu$m diameter) glass fibers formed by melt drawing and pulling, applicable to biological scaffolds.

After holding the melt for a specified time, the melt is converted to continuous fiber form following a number of methods disclosed in the prior art. Fibers may be drawn from the melt by dipping a metal or ceramic rod into the melt, or may be made to flow through a single or multi-holed bushing. The fibers are then drawn down to the desired final diameter, rapidly cooled, and collected on a take-up device.

Prior to collection, the fibers may be coated with a sizing agent, which acts as a protection layer on top of the glass.

The next step is to convert the individual fibers to three-dimensional textile architectures. Textile technologies, such as weaving, braiding, or knitting, may be used to precisely place the fibers in a desired location in space, allowing for a large degree of control in the size and distribution of pores in the bone graft structure. A plurality of fiber types with the same glass composition, each having a different associated resorption rate based upon melt hold time may be formed into a common textile structure with a predetermined spatial distribution of each of said plurality of fiber types. The plurality of different fibers may have approximately the same diameter.

The result is a bioresorbable glass structure for use as bone replacement materials in which pore size and distribution, and the rate of resorption are controlled over a wider range than have been previously reported. The advantages of the present invention over biocompatible inorganic structures disclosed in the past is the ability to both control pore size and distribution for optimized bone ingrowth, and to control the resorption rate of the scaffold by orders of magnitude without having to change the composition of the glass fibers composing the scaffold. The goal is to match the rate of bone growth into the scaffold with the dissolution of the scaffold. In addition, by providing fibers with different resorption rates within the same scaffold, slower resorbing fibers can provide structural support for the scaffold while the faster resorbing fibers promote bone in-growth.

The structures created by this invention may be used as scaffolds for the in vitro or in vivo growth of human or animal tissue, such as bone or cartilage. These scaffolds can be used as implant materials for the replacement of defects or hollow portions of hard tissue resulting from external injury or surgical removal of hard tissue tumors.

Fibers made in accordance with the present invention, may be used in the formation of laminated structures, and a countless number of three-dimensional structures. The individual plies can be formed via textile operations such as weaving, braiding and knitting. Mixed fabric types can be incorporated into the structure for further control of pore size and distribution. Though no optimal pore size and distribution have been established, the size of the pores required for good bone growth is between 100 and 500 microns. The ability to tailor the pore size and distribution is also viewed as a method of enhancing bone growth.

A method in accordance with the present invention for making a hard tissue scaffold for use in repairing an injury to hard tissue, includes the steps of: (a) selecting a glass composition; (b) melting a first amount of the selected glass composition to yield a first glass in a melted state; (c) maintaining the first glass in a melted state for a first melt hold time to confer a first resorption rate to the first glass, the first resorption rate being matched to a predetermined rate of bone growth into the scaffold; (d) forming the first glass into a first resorbable fiber having the first resorption rate; (e) melting a second amount of the selected glass composition to yield a second glass in a melted state; (f) maintaining the second glass in a melted state for a second melt hold time to confer a second resorption rate to the second glass, the second resorption rate being slower than the first resorption rate; (g) forming the second glass into a second resorbable fiber having the second resorption rate; (h) including both the first resorbable fiber and the second resorbable fiber in the hard tissue scaffold, whereby the first resorbable fiber resorbs to promote bone in-growth while the second resorbable fiber persists for a predetermined time in order to maintain structural support for the scaffold.

In addition, the three-dimensional structure may be filled with biological materials, resorbable synthetic polymers, biopolymers or ceramic materials that may or may not contain materials capable of promoting bone growth through the device (three dimensional structure). These include autograft, allograft, or xenograft bone, bone marrow, demineralized bone (DBM), natural or synthetic bone morphogenic proteins (BMP's i.e. BMP 1 through 7), bone morphogenic-like proteins (i.e. growth and differentiation factor 5 (GFD-5) also known as cartilage-derived morphogenic factor 1, GFD-7 and GFD-8) epidermal growth factor (EGF), fibroblast growth factor (FGF i.e. FGF 1 through 9), platelet derived growth factor (PDGF), insulin like growth factor (i.e. IGF-I and IGF-II and optionally IGF binding proteins), transforming growth factors (TGF-$\beta$ i.e. TGF-$\beta$ I through III), vascular endothelial growth factor (VEGF) or other osteoinductive or osteoconductive materials known in the art. Biopolymers could also be used as conductive or chemotactic materials, or as delivery vehicles for growth factors. Examples could be recombinant or animal derived collagen gelatin or elastin. Bioactive coatings or surface treatments could also be applied to the surface of the device. For example, bioactive peptide sequences (RGD's) could be applied to facilitate protein adsorption and subsequent cell tissue attachment. Antibiotics could also be coated on the surface of the device or delivered by a material within the device.

The polymeric materials filling the device could exist in a number of phases including solids, foams, or liquids. The three dimensional structure could be filled with polymer to some specified degree to improve the mechanical toughness of the device. Foamed polymeric materials could be lyophilized within the structure providing a scaffold within a scaffold. The porous polymeric foam would provide an osteoconductive medium for bone growth into the device. The porous foam could also serve as a delivery medium for growth factors, peptides, and other bioactive materials. The three dimensional structure could also be filled with liquid polymers containing biological agents, with the entire structure acting to control the release rate of the agent.

The present invention therefore contemplates a method further including the steps of preparing a resorbable matrix material to combine with the composite textile structure and combining the resorbable matrix material therewith to form the hard tissue scaffold.

The three-dimensional structure could also be filled with photocurable polymeric materials and cured in place with UV light source. It could also be filled with ceramic cements, monolithic ceramic materials or particles that are osteoconductive or inductive. The structure could also be post-processed with a ceramic or polymeric coating that is osteoconductive or inductive. The second ceramic material would act as a coating that would be different from the materials used for the main body of the scaffold.

The three-dimensional, structure may also serve as a scaffold for the engineering of bone tissue to facilitate bone healing. The structure may have an internal porous structure that would be conducive to the growth of cells. As outlined in previous patents (Vacanti, U.S. Pat. No. 5,770,417), tissue can be harvested from a patient and the tissue can be sterile processed to provide a specific cell type (i.e., osteoblast, mesenchymal stem cell (Caplan, U.S. Pat. No. 5,486,359), etc.). The cells could contain inserted DNA encoding a protein that could stimulate the attachment, proliferation or differentiation of bone tissue. The three-dimensional structure would be placed in cell culture and the cells seeded onto or into the structure. The structure would be maintained in a sterile environment and then implanted into the donor patient once the cells have invaded the microstructure of the scaffold. The in vitro seeding of cells could provide for a more rapid healing process. Additionally, radio-opaque markers may be added to the scaffold to allow imaging after implantation.

Without intending to limit it in any manner, the present invention will be more fully described by the following examples.

EXAMPLE 1

Reagent grades of CaO, $Fe_2O_3$, and $P_2O_5$ in a molar ratio of 16.5:33.5:50 were thoroughly mixed to create a batch using a ball mill with high purity zirconia mixing media. The glass was melted in an platinum crucible under a nitrogen atmosphere using an electric furnace. A melt temperature of 1200° C. was sufficient to liquefy the batch. Three melts were created, each with a different hold time above the melt temperature. The hold times were 8, 24, and 48 hours. At the conclusion of the melt cycle, the liquid glass was poured out, or cast, onto steel plates. The glasses quickly solidified, and were stored as cast blocks in desiccators.

To create glass fibers, the glass blocks discussed above were remelted in platinum crucibles under a nitrogen atmosphere using an electric furnace at 900° C., and held until all bubbles had risen to the surface (<1 hour). The melt was transferred to a second electric furnace held at 750° C., and poured from the platinum crucible into a second platinum crucible with a base composed of a single-hole bushing. Under gravity flow, the glass flowed through the bushing, and onto the surface of a rotating drum. The speed of the drum was controlled to create a single filament with a diameter of 15–20 µm. The glass fibers were removed from the drum, and stored in desiccators.

One gram of fibers from each of the melt hold time (8, 24, and 48 hours) batches was placed in one liter plastic containers. At selected times, 10 ml aliquots were removed from the containers, filtered (0.2-µm), and analyzed via DC plasma emission spectroscopy for concentration of calcium and iron.

Table I below displays the concentration of calcium and iron in the PBS versus time for the fibers of the various melt hold times.

TABLE I

Concentration of calcium and iron in PBS solutions versus time for $CaO/Fe_2O_3/P_2O_5$ (molar ratio 16.5/33.5/50) glass fibers with different melt hold times.

| Time in Buffer (hours) | Melt Hold Time (hours) | [Ca] (mg/l) | [Fe] (mg/l) |
|---|---|---|---|
| 0 | 8 | 0.40 | 0.05 |
|  | 24 | 0.40 | 0.05 |
|  | 48 | 0.40 | 0.03 |
| 8 | 8 | 3.51 | 1.77 |
|  | 24 | 0.49 | 0.05 |
|  | 48 | 0.46 | 0.04 |
| 24 | 8 | 9.2 | 5.1 |
|  | 24 | 0.52 | 0.08 |
|  | 48 | 0.50 | 0.06 |
| 168 | 8 | 15.1 | 15.0 |
|  | 24 | 0.79 | 1.58 |
|  | 48 | 0.61 | 0.43 |

The table shows that when corrected for the concentration of calcium and iron in the PBS mix itself, the release rates of both ions from the glass fibers held in the melt state for 24 to 48 hours are over an order of magnitude lower than that of the glass fibers held in the melt state for 8 hours.

EXAMPLE 2

Reagent grades of CaO, $Fe_2O_3$, and $P_2O_5$ in a molar ratio of 33.5:16.5:50 were thoroughly mixed to create a batch using a ball mill with high purity zirconia mixing media. The glass was melted in a platinum crucible under a nitrogen atmosphere using an electric furnace. A melt temperature of 1100° C. was sufficient to liquefy the batch. Two melts were created, each with a different hold time above the melt temperature. The hold times were 8 and 72 hours. At the conclusion of the melt cycle, the liquid glass was poured out, or cast, onto steel plates. The glasses quickly solidified, and were stored as cast blocks in desiccators.

To create glass fibers, the glass blocks discussed above were remelted in platinum crucibles under a nitrogen atmosphere using an electric furnace at 900° C., and held until all bubbles had risen to the surface (<1 hour). The melt was transferred to a second electric furnace held at 750° C., and poured from the platinum crucible into a second platinum crucible with a base composed of a single-hole bushing. Under gravity flow, the glass flowed through the bushing, and onto the surface of a rotating drum. The speed of the drum was controlled to create a single filament with a diameter of 15–20 µm. The glass fibers were removed from the drum, and stored in desiccators.

One gram of fibers from each of the melt hold time (8 and 72 hours) batches was placed in one liter plastic containers. The containers held one liter of phosphate buffered saline solutions (P-3813, Sigma Chemical Co., St. Louis, Mo., mixed as per instructions) which were maintained at physiologic temperature (37° C.) in a water bath. At selected times, 10 ml aliquots were removed from the containers, filtered (0.2-µm), and analyzed via DC plasma emission spectroscopy for concentration of calcium and iron.

Table II below displays the concentration of calcium and iron in the PBS versus time for the fibers of the various melt hold times.

TABLE II

Concentration of calcium and iron in PBS solutions versus time for $CaO/Fe_2O_3/P_2O_5$ (molar ratio 33.5/16.5/50) glass fibers with different melt hold times.

| Time in Buffer (hours) | Melt Hold Time (hours) | [Ca] (mg/l) | [Fe] (mg/l) |
|---|---|---|---|
| 0 | 8 | 0.46 | 0.03 |
|  | 72 | 0.45 | 0.04 |
| 168 | 8 | 21.1 | 13.6 |
|  | 72 | 18.7 | 12.9 |

The table shows that when corrected for the concentration of calcium and iron in the PBS mix itself, the release rates of both ions from the glass fibers held in the melt state for 72 hours are lower than that of the glass fibers held in the melt state for 8 hours.

It will be understood that the embodiment described herein is merely exemplary and that a person skilled in the art may make many variations and modifications without departing from the spirit and scope of the invention. All such variations and modifications are intended to be included within the scope of the invention as defined in the appended claims.

We claim:

1. A method for making a tissue scaffold used in repairing an injury to bone or cartilage, said method comprising the steps of:
   (a) selecting a glass composition for making both a first fiber and a second glass fiber having different resorption rates;
   (b) melting a first amount of the selected glass composition to yield a first glass in a melted state;
   (c) maintaining the first glass in a melted state for a first melt hold time to confer a first resorption rate to the first glass;
   (d) forming the first glass into a first resorbable fiber having the first resorption rate, the first resorption rate being matched to a predetermined rate of bone growth into the scaffold;
   (e) melting a second amount of the selected glass composition from step (a) to yield a second glass in a melted state;
   (f) maintaining the second glass in a melted state for a second melt hold time to confer a second resorption rate to the second glass;
   (g) forming the second glass into a second resorbable fiber having the second resorption rate, the second resorption rate being slower than the first resorption rate;
   (h) including both the first resorbable fiber and the second resorbable fiber having the same glass composition in the bone or cartilage scaffold, whereby the first resorbable fiber resorbs to promote bone in-growth while the second resorbable fiber persists for a predetermined time in order to maintain structural support for the scaffold.

2. The method of claim 1, further including the step of forming the first and the second fibers into a composite textile structure for inclusion in the tissue scaffold.

3. The method of claim 2, wherein the first and second fibers have a diameter in a range of from about 1 $\mu$m to about 100 $\mu$m.

4. The method of claim 2, wherein the glass composition is a phosphate glass composition.

5. The method of claim 4, wherein the glass composition includes CaO, $Fe_2O_3$ and $P_2O_5$ in a molar ratio of approximately 16.5:33.5:50.0.

6. The method of claim 4, wherein the glass composition includes CaO, $Fe_2O_3$ and $P_2O_5$ in approximately the following range of molar ratios (CaO) 16.5 to 33.5: ($Fe_2O_3$) 16.5 to 33.5:($P_2O_5$) 50.0.

7. The method of claim 1, wherein the first melt hold time and the second melt hold time are each in the range of from about 8 hours to about 72 hours.

8. The method of claim 2, wherein said step of forming the composite textile structure results in a spacial distribution of each of the first and second fibers.

9. The method of claim 2, wherein the first and second fibers have approximately the same diameter.

10. The method of claim 2, further including resorbable matrix material the steps of preparing a to combine with the composite textile structure and combining the resorbable matrix material therewith to form the tissue scaffold.

11. The method of claim 10, wherein said matrix material is selected from the group consisting of: resorbable synthetic polymers, bipolymers, ceramics and photocurable polymers.

12. The method of claim 10, further comprising the step of adding bone growth agents to the matrix material.

13. The method of claim 10, further comprising the step of adding a medicament to the matrix to enable controlled release of the medicament.

14. The method of claim 1, further comprising the steps of:
   (i) casting each of the first glass and the second glass into a solid form after the performance of said steps (c) and (f), respectively; and
   (j) remelting said solid form prior to the performance of said steps (d) and (g), respectively.

* * * * *